United States Patent [19]

Naijoh et al.

[11] Patent Number: 5,308,536

[45] Date of Patent: May 3, 1994

[54] OPTICALLY ACTIVE 4-MERCAPTOCINNAMIC ACID DERIVATIVES, PREPARATION METHOD THEREOF AND USE THEREOF

[75] Inventors: Shuichi Naijoh; Ayako Nishioka; Chozo Inoue, all of Tokyo, Japan

[73] Assignee: Showa Denko K.K., Tokyo, Japan

[21] Appl. No.: 89,551

[22] Filed: Jul. 12, 1993

[30] Foreign Application Priority Data

Jul. 10, 1992 [JP] Japan ................................. 4-207150

[51] Int. Cl.$^5$ ...................... C09K 19/52; C09K 19/06; C07C 327/16; G02F 1/13
[52] U.S. Cl. .................... 252/299.01; 252/299.6; 558/252; 558/255; 558/257; 359/104
[58] Field of Search ............ 252/299.01, 299.6, 299.64, 252/299.67; 558/252, 255, 257

[56] References Cited

U.S. PATENT DOCUMENTS

| | | | |
|---|---|---|---|
| 4,751,018 | 6/1988 | Nakauchi et al. | 252/299.64 |
| 5,068,054 | 11/1991 | Betterton et al. | 252/299.62 |
| 5,210,267 | 5/1993 | Chun et al. | 252/299.66 |

*Primary Examiner*—Shean Wu

*Attorney, Agent, or Firm*—Sughrue, Mion, Zinn, Macpeak & Seas

[57] ABSTRACT

An optically active 4-mercaptocinnamic acid derivative represented by general formula (1)

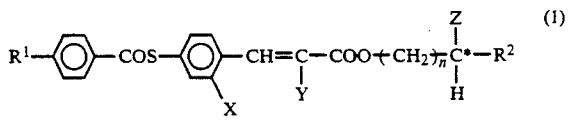

wherein $R^1$ represents an alkyl group, an alkoxy group alkylthio group having 6 to 14 carbon atoms; X is H or F; Y is H or $CH_3$; n is 0 or 1; Z is $CH_3$ or $CF_3$; and $R^2$ represents a $C_{2-8}$ alkyl group, preparation method, bistable or tristable liquid crystal composition containing at least one such derivative, and a liquid crystal display device including such a liquid crystal composition.

The compound of general formula (1) decreases liquid crystal temperature range and broadens it, and enables realizing a bistable or tristable chiral smectic phase. The compound can be used alone or as blended with other liquid crystals having a smectic phase or ferroelectric liquid crystals as a material for liquid crystal devices.

8 Claims, 2 Drawing Sheets

OPTICALLY ACTIVE 4-MERCAPTOCINNAMIC ACID DERIVATIVES, PREPARATION METHOD THEREOF AND USE THEREOF

TECHNICAL FIELD

The present invention relates to novel optically active compounds having a 4-mercaptocinnamic acid structure, production method thereof and use thereof. More particularly, the present invention relates to ferroelectric liquid crystal compounds having bistability and their compositions, chiral smectic liquid crystal compounds exhibiting tristability and their compositions, and liquid crystal devices utilizing responses to electric field of these liquid crystal compositions.

BACKGROUND ART

Liquid crystal display devices utilizing response of liquid crystals to electric field which have heretofore been developed and put into practice include those using so-called nematic liquid crystal compounds which can be categorized in DSM, TN, STN types, etc., or compositions containing these compounds.

However, those using nematic liquid crystals have a defect that their response time is very long, e.g., several milliseconds, and hence, it is said that attempts to increase in the size of the display screen has been reaching a limitation. Since the response of a nematic liquid crystal to an applied electric field is fundamentally based on anisotropy of dielectric constant of the liquid crystal molecule, its driving torque is small and response time is long.

Among the conventional nematic liquid crystal devices, chiral smectic liquid crystals developed by R.B. Meyer et al. show ferroelectricity and enable high speed response on the order of several micro seconds utilizing a large driving torque as expressed by direct interaction $P_s \times E$ between spontaneous polarization ($P_s$) and applied electric field (E) (J. Physique, 36, L-69 (1975)). These chiral smectic liquid crystals, which are called ferroelectric liquid crystals, exhibit their function in a series of smectic phases tilted away from a smectic layer normal. Recently, a vigorous development has been made on, among others, chiral smectic C phase (hereinafter, referred to as "$S_c*$" for short), which is appraised of superiority in practice because of its low viscosity.

As a typical example of a display device utilizing a ferroelectric liquid crystal, N.A. Clark and S.T. Lagerwall (Japanese Patent Application Laid-open No. 107216/1981; U.S. Pat. No. 4,367,924) proposed a liquid crystal display device using a liquid crystal having bistability, in which the spiral axis is parallel and layers are perpendicular to the substrate, and the spiral structure is made to disappear to generate a stabilized polarized domain on the surface, and orientation of the molecules is changed by polarity of the applied electric field.

However, it has been clarified that in spite of development of several thousands kinds of ferroelectric liquid crystal compounds and compositions having a Sc* phase, there are still problems which follow:

(1) There exists no clear, sharp direct current threshold, and dynamic driving is difficult;
(2) There occurs incomplete switching or seizing due to presence of spontaneous polarization;
(3) The orientation of the compounds is susceptible to mechanical impacts and tends to be readily broken.
(4) There occurs decrease in contrast ratio due to twisted orientation called twist or deformation of smectic layer called chevron structure; and so on.

Therefore, there has been a demand for liquid crystal display devices which utilize effectively large direct interaction between spontaneous polarization and applied electric field and have high speed response to the applied field. However, no practically usable liquid crystal of such a type has been realized.

In 1988, A.D.L. Chandani et al. proposed a switching having tristability which utilizes a third state and two uniform states using 4-(1-methylheptyloxycarbonylphenyl) 4'-octylbiphenyl -4-carboxylate (MHPOBC) (Jpn. J. Appl. Phys., 27, L729 (1988)).

Recently, it has been found that the third state is an antiferroelectric chiral smectic phase, and tristable switching is phase transition between an electric field induced ferroelectric phase and an antiferroelectric phase.

Tristable switching differs from the aforementioned bistable switching of ferroelectric liquid crystal in:

(1) Orientation is easy and the device has a function of self-restoring defects;
(2) There exist a clear direct current threshold and hysteresis;
(3) There occurs no seizing or turbulence in orientation due to spontaneous polarization in the absence of electric field; and so on.

However, few tristable switching liquid crystal compound (antiferroelectric liquid crystal) hitherto found are practically usable since they have defects which follow.

1) Most of them have a ring structure such as biphenyl, naphthyl, dioxolanephenyl, cyclohexylphenyl or phenylpyrimidyl as a skeleton, and all but one exception (the compound disclosed in Japanese Patent Application Laid-open No. 218337/1991) contain three or more aromatic or aliphatic rings, and hence, have high liquid crystal temperature ranges in which they exhibit tristability (Jisedai Ekisho Disupurei to Ekisho Zairyo (Liquid Crystal Display of Next Generation and Liquid Crystal Materials), 287-336 (1992), CMC Corporation).

2) Most of them have ester bonds as bonding between ring structures. Liquid crystals having ester bonds are known to generally have high viscosity, and for this reason the conventional compounds are considered to have long response time for tristable switching which involves generation and growth of domains.

3) Although methylene oxide bonds instead of ester bonds have been studied with view to reduction of viscosity, the use of methylene oxide bonds deteriorates liquid crystal property and fails to give a broad liquid crystal range.

Therefore, it has been desired to develop liquid crystal compound and composition obviating the aforementioned defects and exhibit excellent tristability.

SUMMARY OF INVENTION

Therefore, an object of the present invention is to develop liquid crystal compounds which have tristability within a broad temperature range including room temperature and which are expected to be low in viscosity from their structure, and provide novel liquid crystal compounds which can be used in liquid crystal display devices utilizing tristable switching.

Another object of the present invention is to provide novel liquid crystal compounds which can be used not only alone but also as liquid crystal compositions containing a mixture of a plurality of compounds or a mixture with one or more other liquid crystal compounds in liquid crystal display devices utilizing tristable switching.

A further object of the present invention is to provide novel ferroelectric liquid crystal compounds enabling bistable switching and novel liquid crystal compositions containing mixture of a plurality of such liquid crystal compounds or a mixture with one or more other liquid crystal compounds.

The present inventors have made intensive investigation without sticking to the molecular structure of the conventional ferroelectric liquid crystals or tristable liquid crystals, and as a result, have obtained a molecular design concept that two-aromatic rings having a cinnamic acid structure are effective for decreasing and broadening the liquid crystal temperature range, and introduction of thioester bonds instead of ester bonds further improves temperature range and viscosity. Further, the present inventors have found that change in the structure of optically active sites enables to exhibiting bistability or tristability. The present invention has been completed based on these discoveries.

DISCLOSURE OF INVENTION

The compounds provided by the present invention are optically active 4-mercaptocinnamic acid derivatives each containing, as a mesogen (basic structure), 4-mercaptocinnamic acid, i.e., cinnamic acid having a mercapto group introduced at the p-position, whose mercapto group and carbonyloxy group are bonded to a 4-substituted benzoyl group and an alkyl group, respectively, the derivatives being represented by general formula (1) below:

wherein $R^1$ represents an alkyl group, an alkoxy group or an alkylthio group having 6 to 14 carbon atoms; X represents a hydrogen atom or a fluorine atom; Y represents a hydrogen atom or a methyl group; n is 0 or 1; Z represents a methyl group or a trifluoromethyl group; and $R^2$ represents an alkyl group having 2 to 8 carbon atoms.

Those compounds corresponding to the compounds of the present invention represented by general formula (1) above in which the thioester bonds are replaced by ester bonds are disclosed in Japanese Patent Application Laid-open No. 239250/1988., and some of them reportedly exhibit ferroelectricity. However, these compounds are quite different from the compounds of the present invention in that they have no thioester bond structure, nor exhibit antiferroelectricity (tristability).

Besides, while the compounds having thioester bond of the present invention shows liquid cristal property in a broad temperature range as a single substance, most of the compounds having ester bond disclosed in the prior art do not show liquid cristal property by a single substance itself. Even if there should be the compounds that show liquid cristal property, the temperature range within which liquid cristal property appears is extremely narrow. Furthermore, its liquid cristal property is monotropic where the property only emerges as lowering the temperature and does not emerge as rising the temperature.

The compounds of the present invention represented by general formula (1) above can be prepared by the following two methods according to the present invention.

First preparation method is to condense a compound as represented by general formula (4)

wherein $R^1$ represents an alkyl group, an alkoxy group or an alkylthio group having 6 to 14 carbon atoms, or its reactive derivative, with a compound represented by general formula (6)

wherein X represents a hydrogen atom or a fluorine atom; and Y represents a hydrogen atom or a methyl group, to form a compound represented by general formula (2)

wherein the symbols have the same meanings as defined above, and condense the compound represented by general formula (2) or its reactive derivative with an optically active compound represented by general formula (3)

wherein n is 0 or 1; Z represents a methyl group or a trifluoromethyl group; and $R^2$ represents an alkyl group having 2 to 8 carbon atoms.

Second preparation method is to condense a compound represented by general formula (6)

wherein X and Y have the same meanings as defined above, or its reactive derivative, with an optically active compound represented by general formula (3)

wherein n, Z and $R^2$ have the same meanings as defined above, to obtain a compound represented by general formula (5)

wherein X, Y, Z, n and $R^2$ have the same meanings as defined above, and then condense the compound represented by general formula (5) with a compound represented by general formula (4)

wherein $R^1$ represents an alkyl group, an alkoxy group or an alkylthio group having 6 to 14 carbon atoms, or its reactive derivative.

As for the starting compounds used in the preparation method of the present invention, the substituent $R^1$ in the compounds represented by general formula (4) contains having 6 or more carbon atoms for broadening the liquid crystal temperature range and is an alkyl group (for example, hexyl, heptyl, octyl, nonyl, decyl, undecyl, dodecyl, tridecyl, tetradecyl, etc.), an alkoxy group (for example, hexyloxy, heptyloxy, oxtyloxy, nonyloxy, decyloxy, undecyloxy, dodecyloxy, tridecyloxy, tetradecyloxy, etc.), and an alkylthio group (for example, hexylthio, heptylthio, octylthio, nonylthio, decylthio, undecylthio, dodecylthio, tridecylthio, tetradecylthio, etc.).

The compounds of the present invention represented by formula (4) are known per se, and can be prepared by conventional method from hydroxybenzoic acid and corresponding halogenated alkyl. Also, commercial product may be obtained.

The compounds represented by general formula (3) are optically active alcohols having asymmetric carbon atoms, respectively. Such asymmetric carbon-containing optically active alcohols can be obtained as by-product in alcohol fermentation, and commercially available. Among them, those optically active alcohols are preferred in which $R^2$ is ethyl, propyl, pentyl or hexyl; and Z is methyl or trifluoromethyl, which can be obtained with ease.

The 4-mercaptocinnamic acid compounds represented by general formula (6) can be prepared, for example, by obtaining a 4-chlorosulfonylcinnamic acid derivative from a corresponding cinnamic acid derivative and chlorosulfonic acid, followed by reduction with a reducing agent (stannous chloride, etc.).

(i) Condensation reaction of the compound represented by general formula (2) or its reactive derivative with the compound represented by general formula (3), and (ii) condensation reaction of the compound represented by general formula (4) or its reactive derivative with the compound represented by general formula (5) are performed by a conventional method generally known as a method for synthesizing ester compounds from an organic carboxylic acid or its reactive derivative and an organic alcohol. As the reactive derivative, there can be cited acid halides such as acid chlorides, which can be readily prepared with thionyl chloride.

In either of the preparation methods (i) and (ii) above, the reaction is conducted in a suitable solvent, for example, ethyl acetate, toluene, ethyl ether, tetrahydrofuran, dichloromethane, hexane, etc. in the presence of a condensing agent. As the condensing agent, there can be cited dicyclohexylcarbodiimide, etc.

For example, the mercaptocinnamic acid derivative represented by general formula (5) and the optically active alcohol represented by general formula (3) are added in the aforementioned solvent in the presence of dicyclohexylcarbodiimide or the like as a condensing agent, and reacted at room temperature or under ice cooling with stirring. Then, the solvent is distilled off, and the residue is stirred in a suitable solvent to filter insoluble matter, which is dried over anhydrous magnesium sulfate. After distilling off the solvent, the residue is separated by silica gel column chromatography using a suitable eluent to obtain the objective compound.

When an acid halide is used as the reactive derivative, the reaction is conducted in the presence of a dehydrohalogenating agent (organic base such as dry pyridine, etc.).

For example, when the acid halide represented by general formula (2) as the reactive derivative and the optically active alcohol represented by general formula (3), heat reaction is conducted in the presence of a dehydrohalogenating agent (organic base such as dry pyridine, etc.), the reaction mixture is extracted with a solvent such as ether, the ether layer is washed with water and then with saturated saline, dried over anhydrous magnesium sulfate, and the solvent is distilled off, followed by purification by silica gel column chromatography to obtain the objective compound.

ADVANTAGEOUS EFFECTS OF THE INVENTION

As described above, optically active 4-mercaptocinnamic acid derivatives represented by general formula (1), which are novel liquid crystal compounds of the present invention can be readily prepared by the methods of the present invention.

The liquid crystal compounds of the present invention are 4-mercaptocinnamic acid derivatives having a thioester group and an optically active group through a cinnamic acid structure, and the introduction of two-aromatic rings having a cinnamic acid structure and of a thioester bond in the molecule enables decreasing and broadening liquid crystal temperature as will be apparent from examples described hereinbelow. Further, change in the structure of optically active site enables generation of a chiral smectic phase having bistability or tristability.

The liquid crystal compounds of the present invention exhibit bistability (ferroelectricity) or tristability (antiferroelectricity) in a temperature range including room temperature. Therefore, not only they can be used alone but also they can be blended with other liquid crystals having a smectic phase or ferroelectric liquid crystals to give materials for liquid crystal devices utilizing electrooptical effects within practical temperature ranges.

Blending the liquid crystal compounds of the present invention with ferroelectric liquid crystal compounds or compositions having bistability or with liquid crystals having a smectic phase enables broadening temperature ranges in which bistability or tristability is exhibited or improvement of responsibility, so that they can be applied to liquid crystal devices utilizing bistable switching and tristable switching. Thus, the liquid crystal compounds of the present invention are very useful liquid crystal material.

BEST MODE FOR CARRYING OUT THE INVENTION

Hereinafter, the present invention will be described in more detail by examples. However, the present invention should not be construed as being limited thereto.

Hereinafter, symbols used have the following meanings.

Cry: Crystals;
Sx: Smectic phase difficult to be identified;
$S_{ca}^*$: Chiral smectic phase showing tristability;
$S_c^*$: Chiral smectic phase showing bistability;
Sa: Smectic A phase;
Ch: Cholesteric phase;
Iso: Isotropic phase.

In the following examples, (R) forms and (S) forms used are optically active compounds (optical purity: 99%). However, the compounds of the present invention are not limited to those having an optical purity within a specified range. Note that phase transition point and physical constants may be slightly influenced by purity. For example, phase transition point sometimes differ by about 1° C.

EXAMPLE 1

Synthesis of (R)-1-methylheptyl trans-(4-(4'-decyloxybenzoyl)mercapto) -cinnamate

1-1: Synthesis of Trans-(4-Chlorosulfonyl)Cinnamic Acid

A 3,000 ml three-necked flask equipped with a stirrer, thermometer and a calcium chloride feed pipe was charged with 600 g of chlorosulfonic acid, and heated to 40° C. with stirring. Then, while stirring the solution, 148 g of trans-cinnamic acid was added dropwise. On this occasion, hydrochloric acid gas was generated with heat generation, and hence, the reaction mixture was stirred on an ice bath so as to keep the temperature of the reaction mixture to 50° to 55° C. After completion of the dropwise addition over 20 minutes, stirring was continued for additional 45 minutes with keeping the temperature at 50° to 55° C. Then, the resulting reddish brown reaction mixture was left to stand, the reaction mixture was poured onto 2 kg of ice while keeping the temperature to 10° C. or lower. The solution obtained was filtered and the solids were washed several times each with 100 ml of ice water, and dried under vacuum over one night. The crude product was recrystallized from 2,000 ml of hot acetic acid to obtain 52.0 g of colorless plates (yield: 21%, melting point: 223° C.).

1-2: Synthesis of Trans-(4-Mercapto)Cinnamic Acid

A 2,000 ml three-necked flask equipped with a stirrer, a nitrogen gas introduction pipe and a reflux condenser was charged with 700 ml of ethyl alcohol, and then 51.2 g of trans-(4-chlorosulfonyl)cinnamic acid synthesized in Example 1-1 above, and nitrogen gas was introduced in the flask for 5 minutes to purge the flask with nitrogen. Then, while stirring the solution, 250 ml of concentrated hydrochloric acid and then 200 g of anhydrous stannous chloride were added. After completion of the addition, the reaction mixture was heated under reflux for 30 minutes.

Then, the reaction mixture was poured in an aqueous hydrochloric acid solution (concentrated hydrochloric acid:cold water=1:1 (v/v)), and the solution obtained was filtered to obtain yellow solids, which were washed with 100 ml of concentrated hydrochloric acid and then 100 ml of water several times, respectively. The crude product thus obtained was dissolved in 300 ml of an aqueous 10% sodium hydroxide solution, and stirred for 3 minutes, followed by filtering insoluble matter. Hydrochloric acid was added to the aqueous alkali solution to render it litmus acidic to precipitate crystals, which were filtered. The crystals thus obtained were washed with water and then with hexane several times, respectively, and then dried under vacuum to obtain 22.5 g of yellow powder (yield: 60%, melting point: 217° C.). Note that the above-mentioned procedure was conducted in a nitrogen atmosphere.

1-3: Synthesis of Trans-(4-(4'-Decyloxybenzoyl)Mercapto)Cinnamic acid

A 3,000 ml two-necked flask equipped with a stirrer and a reflux condenser was charged with 500 ml of thionyl chloride and 277 g of 4-n-decyloxybenzoic acid obtained by a conventional method, and stirred together with 0.1 g of dimethylformamide at room temperature over one night. Thereafter, the mixture was heated for 1 hour under reflux. Then, unreacted thionyl chloride was removed under reduced pressure to obtain 293 g of 4-decyloxybenzoyl chloride as a colorless to yellow oily product (yield: 99%, boiling point: 175° to 180° C./0.5 mmHg).

Next, a 500 ml three-necked flask equipped with a stirrer, and a nitrogen gas introduction pipe was charged in a nitrogen atmosphere with an aqueous alkali solution having dissolved 9.0 g of potassium hydroxide in 50 ml of water and 10.8 g of 4 mercapto-trans-cinnamic acid synthesized in Example 1-2 above, and the reaction mixture was stirred until it turned yellow and transparent. Further, 200 ml of ethyl alcohol was added, and then 41.5 g of 4-decyloxybenzoyl chloride slowly while stirring in a nitrogen atmosphere. After completion of the reaction, 50 ml of water was added and crystals formed were filtered, which were then suspended in 500 ml of water and stirred at 60° to 70° C. for 5 minutes. The mixture was filtered and crystals were suspended in 250 ml of acetone and filtered to obtain 17.5 g of the objective compound as colorless powder (yield: 66%, melting point 254° C.).

1-4: Synthesis of (R)-1-Methylheptyl Trans-(4-(4'-Decyloxybenzoyl)Mercapto)Cinnamate A 300 ml two-necked flask equipped with a stirrer and a reflux condenser was charged with 50 ml of thionyl chloride and 8.8 g of trans-(4-(4'-decyloxybenzoyl)-mercapto)cinnamic acid obtained in Example 1-3 above, and heated under reflux for 1 hour together with 0.01 g of dimethylformamide. Then, unreacted thionyl chloride was removed under reduced pressure to obtain 8.8 g of trans-(4-(4'-decyloxybenzoyl)mercapto)cinnamyl chloride.

This was added to a solution of 10.4 g of (R)-(−)-2-octanol in 60 ml of dry pyridine with stirring, and the mixture was stirred at 55° to 65° C. over one night. After the reaction mixture was cooled and 450 ml of 4N hydrochloric acid was added thereto, the mixture was extracted with ether. The ether layer was washed with water and then with saturated saline, and dried over anhydrous magnesium sulfate. After distilling off the solvent, the residue was purified by silica gel column chromatography using a petroleum ether/dichloromethane based eluent to obtain 5.0 g (yield: 45%).

$^1$H-NMR (ppm): 7.99(d,2H), 7.68(d,1H), 7.59(d,2H), 7.52(d,2H), 6.95(d,2H), 6.47(d,1H), 5.05(tq,1H), 4.03(t,2H), 0.89–1.82(35H).

Measurement of Phase Transition Temperature

The compound thus obtained was measured for phase transition temperature, and results obtained are shown. The phase transition temperature was judged by visual observation using a polarizing microscope with a stage for heating and cooling and by differential scanning calorimeter.

$$Cry \xrightarrow{<r.t.} Sca^* \xrightarrow{52°\ C.} Sa \xrightarrow{70°\ C.} Iso$$

r.t. room temperature

Measurement of Spontaneous Polarization and Change in Light Transmittance

The compound obtained was heated to form an anisotropic liquid, which was poured between a space defined by two glass substrates (distance: 3.5 microns) having transparent electrodes, respectively, through a spacer to fabricate a thin liquid crystal cell. Then, the cell was cooled slowly to obtain a mono domain of an Sa phase in which molecular directions are oriented uniformly, and further cooled slowly to obtain an Sca* phase. The liquid crystal cell thus obtained was arranged under a polarizing microscope having a light receptor and two polarizers crossed at right angles so that angle of a molecular direction with respect to the polarizer under no applied electric field became 22.5°. In this condition, spontaneous polarization and light transmittance were measured by a triangular wave voltage application method (50 Vpp, 10 Hz).

Figure 1:
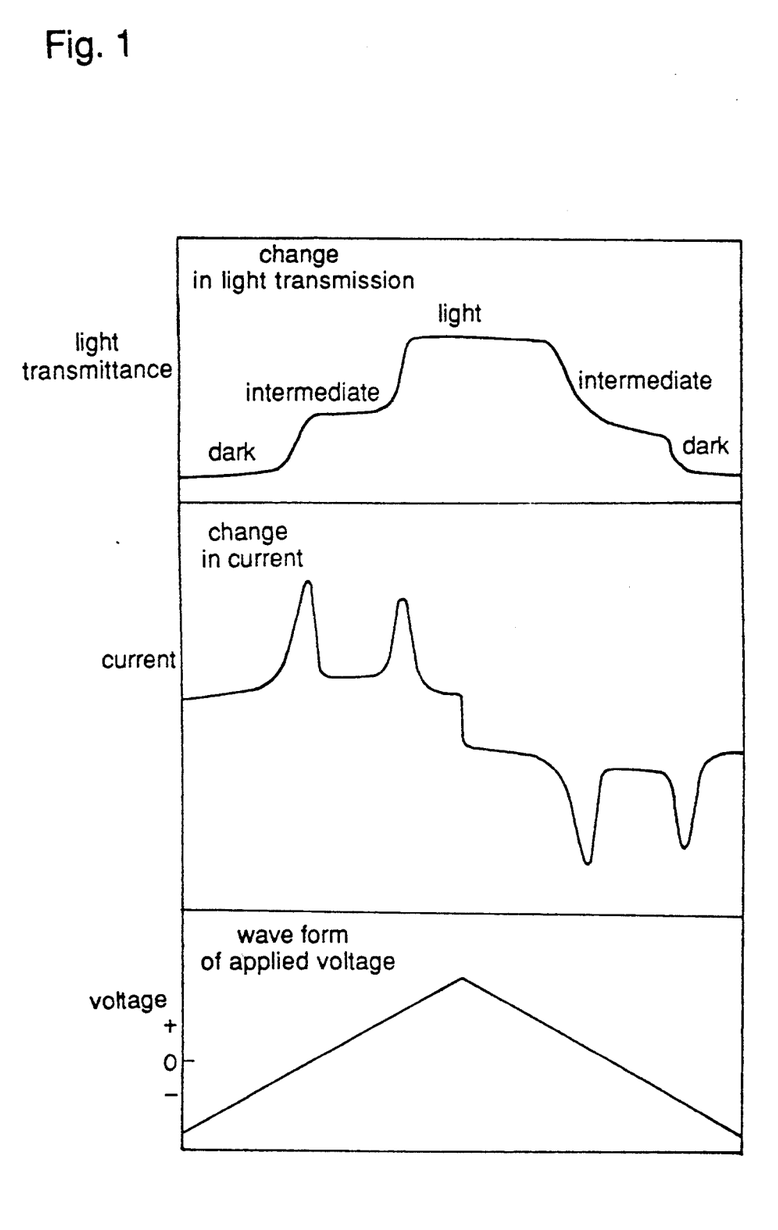
FIG. 1 is a graph illustrating results of measurements of changes in transmittance of light and electric current when the triangular wave voltage is applied to liquid crystal compound of Example 1.

Spontaneous polarization measured was 35 nC/cm$^2$ (35° C.). Results of changes in light transmittance and current are shown in FIG. 1. In addition to a dark state under application of negative voltage and a light state under application of positive voltage, there was clearly observed an intermediate state in a 0 volt region, which confirmed that the liquid crystal molecule had three stable orientations.

EXAMPLE 2

Synthesis of (S)-2-Methylbutyl Trans-(4-(4'-Decyloxybenzoyl)Mercapto)-α-Methylcinnamate

2-1: Synthesis of trans-(4-chlorosulfonyl)-α-methylcinnamate

A 3,000 ml three-necked flask equipped with a stirrer, thermometer and a calcium chloride feed pipe was charged with 1,500 g of chlorosulfonic acid, and heated to 40° C. with stirring. Then, while stirring, 300 g of trans-α-methylcinnamic acid was added dropwise with stirring. On this occasion, since hydrochloric acid gas was generated with heat generation, the reaction mixture was stirred on an ice bath so as to keep the temperature of the reaction mixture to 50° to 55° C. After completion of the dropwise addition over 25 minutes, the stirring was continued for additional 40 minutes with keeping the temperature at 50° to 55° C.

Next, the resulting reddish brown reaction mixture was cooled down to 10° C. or lower, the reaction mixture was poured onto 2 kg of ice slowly and stirred. After the reaction mixture was filtered, the solids obtained were washed several times each with 100 ml of ice water. The solids were dissolved in 1,000 ml of hot acetone and stirred for a while. Then the solution was cooled down to −5° C. and filtered. The crystals obtained were washed several times each with 100 ml of cold hexane, and dried under vacuum to obtain 298 g of trans-(4-chlorosulfonyl)-α-methylcinnamic acid (yield: 62%, melting point: 190° C.).

2-2: Synthesis of Trans-(4-Mercapto)-α-Methylcinnamic Acid

A 1,000 ml three-necked flask equipped with a stirrer, a nitrogen gas introduction pipe and a reflux condenser was charged with 250 ml of ethyl alcohol, and then 26 g of trans-(4-chlorosulfonyl)-α-methylcinnamic acid synthesized in Example 2-1 above, and the flask was purged with nitrogen gas. Thereafter, while stirring the solution, 150 ml of concentrated hydrochloric acid and then 136 g of stannous chloride (dihydrate) were added, and the reaction mixture was heated under reflux for 25 minutes. Then, the reaction mixture was poured in a cold aqueous 6M hydrochloric acid solution. The yellow crystals obtained by filtration were washed with concentrated hydrochloric acid, water and hexane several times, respectively, and then recrystallized from 50 ml of toluene to obtain 8.6 g of the objective compound (yield: 44%, melting point: 159° C.). The above-described procedure was carried out in a nitrogen atmosphere.

2-3: Synthesis of Trans-(4-(4'-Decyloxybenzoyl)Mercapto)-α-methylcinnamic acid A 300 ml two-necked flask equipped with a stirrer and a reflux condenser was charged with 100 ml of carbon tetrachloride, 4.5 ml of thionyl chloride and 11.1 g of 4-n-decyloxybenzoic acid obtained by a conventional method, and heated under reflux together with one drop of dimethylformamide for 4 hours. Then, unreacted thionyl chloride was removed under reduced pressure to obtain 4-decyloxybenzoyl chloride as a colorless liquid.

Next, a 500 ml three-necked flask equipped with a stirrer, and a nitrogen gas introduction pipe was charged in a nitrogen atmosphere with an aqueous alkali solution having dissolved 2.2 g of potassium hydroxide in 20 ml of water and 3.88 g of trans-(4-mercapto)-α-methylcinnamic acid synthesized in Example 2-2 above, and the reaction mixture was stirred until it turned yellow and transparent. Further, 80 ml of ethyl alcohol was added, and while stirring the mixture in a nitrogen atmosphere, the 4decyloxybenzoyl chloride obtained previously was added slowly. After stirring for a while, 300 ml of water was added and it was confirmed that the solution was litmus acidic, followed by filtering crystals formed. The crystals were suspended in 200 ml of water and stirred at 60° to 70° C. for 5 minutes, and the crystals were filtered, washed with a small amount of acetone, and dried to obtain 5.0 g of the objective compound as colorless powder (yield: 55%).

2-4: Synthesis of (S)-2-Methylbutyl Trans-(4-(4'-decyloxybenzoyl) mercapto)-α-methylcinnamate Trans-(4-(4'-decyloxybenzoyl)mercapto)-α-methylcinnamate obtained in Example 2-3 above (2.0 g) and 0.47 g of S-(−)-2-methyl-1-butanol were added to 20 ml of dichloromethane, and further 1.0 g of dicyclohexylcarbodiimide and 0.07 g of 4-pyrrolidinopyridine were added thereto. The mixture was stirred at room temperature for 18 hours. After the solvent was removed under reduced pressure, 50 ml of ethyl acetate was added, and the mixture was stirred for a while. After insoluble matter was filtered, the ethyl acetate layer was washed with 50 ml of water and then with 50 ml of saturated saline, and dried over anhydrous magnesium sulfate. The ethyl acetate was distilled off and the residue was separated by silica gel column chromatography using n-hexane/ethyl acetate based eluent to obtain 1.45 g of (S)-2-methylbutyl trans-(4-(4'-decyloxybenzoyl) mercapto)-α-methylcinnamate as colorless crystals (yield: 63%).

$^1$H-NMR (ppm): 8.00(d,2H), 7.66(s,1H), 7.54(d,2H), 7.44(d,2H), 6.94(d,2H), 4.02(td,4H), 2.11(s,3H), 0.89–1.83(28H).

Measurement of Phase Transition Temperature

The compound thus obtained was measured for phase transition temperature in the same manner as in Example 1, and results obtained are shown below.

$$\text{Cry} \xrightarrow{5°\text{ C.}} \text{Sc}^* \xrightarrow{57°\text{ C.}} \text{Sa} \xrightarrow{91°\text{ C.}} \text{Iso}$$

Measurement of Spontaneous Polarization and Change in Light Transmittance

The compound obtained was measured for spontaneous polarization and change in light transmittance by applying triangular wave voltage (50 Vpp, 10 Hz) in the same manner as in Example 1.

Figure 2:
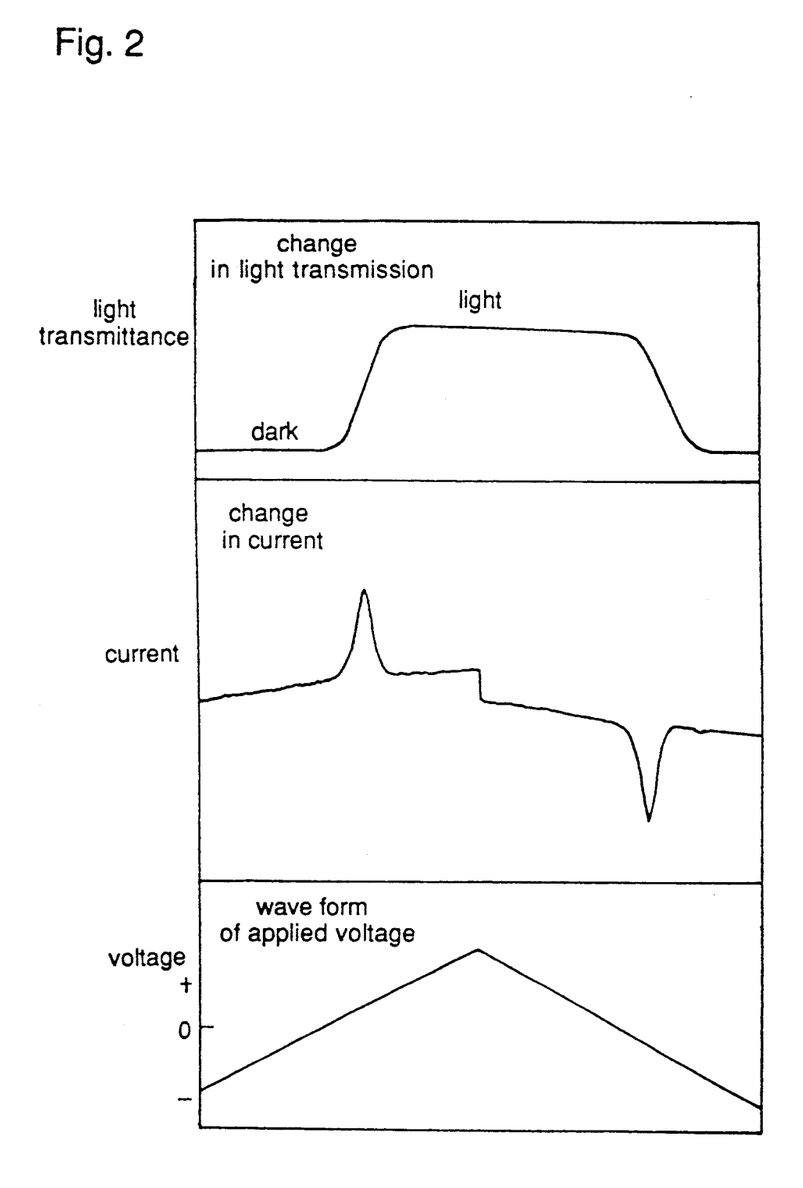
FIG. 2 is a graph illustrating results of measurements of changes in transmittance of light and electric current when the triangular wave voltage is applied to liquid crystal compound of Example 2.

Spontaneous polarization measured was 4 nC/cm$^2$ (25° C.). Results of changes in light transmittance and current are shown in FIG. 2. There were observed a dark state under application of negative voltage and a light state under application of positive voltage.

EXAMPLE 3

Synthesis of (R)-1-Methylheptyl Trans-(4-(4'-Decylthiobenzoyl) Mercapto)-α-Methylcinnamate 3-1:

The same reaction as in Example 2-3 was carried out except that 12.1 g of 4-n-decylthiobenzoic acid was used in place of 11.1 g of 4-n-decyloxybenzoic acid to obtain 3.76 g of trans-(4-(4'-decylthiobenzoyl)mercapto)-α-methylcinnamic acid (yield: 40%).

3-2:

The same reaction as in Example 2-4 was carried out except that 2.0 g of trans-(4-(4'-decyloxybenzoyl)mercapto)-α-methylcinnamic acid was replaced by 4.7 g of trans-(4-(4'-decylthiobenzoyl) mercapto)-α-methylcinnamic acid synthesized in Example 3-1, 4.7 g of (S)-(−)-2-methyl-1-butanol was replaced by 1.56 g of (R)-(−)-2-octanol, and the charge amount of dicyclohexylcarbodiimide was changed to 2.27 g to obtain 3.27 g of (R) 1 methylheptyl trans-(4-(4'-decylthiobenzoyl) mercapto)-α-methylcinnamate (yield: 56%).

The compound obtained was measured for phase transition temperature in the same manner as in Example 1. Result obtained is shown in Table 1.

EXAMPLES 4 to 10

In the same manner as in Examples 1 to 3, compounds of Examples 4 to 10 were synthesized which corresponded to general formula (1) below (1)

wherein X, Y, Z and R$^2$ are groups as shown in Table 1. $^1$H-NMR analysis confirmed that the compounds obtained had the objective structures.

These compounds were measured for phase transition temperature and spontaneous polarization in the same manner as in Example 1 (temperatures for the measurement of spontaneous polarization were 45° C. in Example 4, 35° C. in Examples 5 to 9, and 25° C. in Example 10). Results of measurements are shown in Table 1 together with results in Examples 1 to 3.

TABLE 1

| Example | R$^1$ | X | Y | Z | n | R$^2$ | Phase transition temperature (°C.) | Sp. p* |
|---|---|---|---|---|---|---|---|---|
| 1 | C$_{10}$H$_{21}$O | H | H | CH$_3$ | 0 | C$_6$H$_{13}$ | Cry $\xrightarrow{<\text{r.t.}}$ Sca* $\xrightarrow{52°\text{ C.}}$ Sa $\xrightarrow{70°\text{ C.}}$ Iso | 35 |
| 2 | C$_{10}$H$_{21}$O | H | CH$_3$ | CH$_3$ | 1 | C$_2$H$_5$ | Cry $\xrightarrow{5°\text{ C.}}$ Sc* $\xrightarrow{57°\text{ C.}}$ Sa $\xrightarrow{91°\text{ C.}}$ Iso | 4 |
| 3 | C$_{10}$H$_{21}$S | H | CH$_3$ | CH$_3$ | 0 | C$_6$H$_{13}$ | Cry $\xrightarrow{25°\text{ C.}}$ Sa $\xrightarrow{44°\text{ C.}}$ Iso | — |
| 4 | C$_{10}$H$_{21}$O | H | H | CH$_3$ | 1 | C$_2$H$_5$ | Sx $\xrightarrow{45°\text{ C.}}$ Sc* $\xrightarrow{68°\text{ C.}}$ Sa $\xrightarrow{112°\text{ C.}}$ Iso | 1 |
| 5 | C$_{10}$H$_{21}$O | H | H | CH$_3$ | 0 | C$_3$H$_7$ | Cry $\xrightarrow{34°\text{ C.}}$ Sca* $\xrightarrow{51°\text{ C.}}$ Sa $\xrightarrow{86°\text{ C.}}$ Iso | 36 |

TABLE 1-continued

| Example | R¹ | X | Y | Z | n | R² | Phase transition temperature (°C.) | Sp. p* |
|---|---|---|---|---|---|---|---|---|
| 6 | $C_{10}H_{21}O$ | F | H | $CH_3$ | 1 | $C_2H_5$ | Cry $\xrightarrow{68° C.}$ Iso | — |
| 7 | $C_{10}H_{21}O$ | F | H | $CH_3$ | 0 | $C_3H_7$ | Cry $\xrightarrow{45° C.}$ Iso | — |
| 8 | $C_{10}H_{21}O$ | F | H | $CH_3$ | 0 | $C_6H_{13}$ | Cry $\xrightarrow{48° C.}$ Iso | — |
| 9 | $C_{10}H_{21}O$ | H | $CH_3$ | $CH_3$ | 0 | $C_6H_{13}$ | Cry $\xrightarrow{14° C.}$ Sc* $\xrightarrow{40° C.}$ Sa $\xrightarrow{55° C.}$ Iso | 72 |
| 10 | $C_{10}H_{21}O$ | H | $CH_3$ | $CF_3$ | 0 | $C_6H_{13}$ | Cry $\xrightarrow{16° C.}$ Sc* $\xrightarrow{32° C.}$ Sa $\xrightarrow{41° C.}$ Iso | 1 |

*Spontaneous polarization: $nC/cm^2$

EXAMPLE 11

As a representative example of compounds which exhibit no bistability (ferroelectricity) nor tristability as simple compound, a liquid crystal having a phenyl pyrimidine skeleton having an Sc phase, represented by formula (A) below (A)

and having phase transition temperature below $$Sx \xrightarrow{36° C.} Sc \xrightarrow{62° C.} Sa \xrightarrow{76° C.} Iso$$

was selected, and 80% by weight of the compound of Example 1 was mixed with 20% by weight of the liquid crystal. The composition thus obtained had a spontaneous polarization of 9 nC/cm² (25° C.), and a phase transition temperature below:

$$Cry \xrightarrow{\leq 0° C.} Sca* \xrightarrow{38° C.} Sa \xrightarrow{74° C.} Iso$$

The liquid crystal composition exhibited an Sca* phase over a broad temperature range. The spontaneous polarization and change in light transmittance were measured in the same manner as in Example 1. As a result, it was confirmed that like in Example 1, the composition had three stable orientations of liquid crystal molecule. This makes it possible to use it in admixture with conventional liquid crystal compounds or compositions having an Sc phase.

EXAMPLE 12

A liquid crystal composition was prepared which was composed of 50 parts by weight of the compound of Example 4 and 25 parts by weight of the compounds of Examples 1 and 5, respectively, and was measured for phase transition temperature and spontaneous polarization under application of 30 Vpp, 50 Hz rectangular wave using the same cell as used in Example 1. As a result, clear bistable switching was observed. The composition had the following phase transition temperature:

$$Sx \xrightarrow{4° C.} Sc* \xrightarrow{57° C.} Sa \xrightarrow{94° C.} Iso$$

and a spontaneous polarization of 18 nC/cm² (17° C.).

We claim:

1. An optically active 4-mercaptocinnamic acid derivative represented by general formula (1)

wherein R¹ represents an alkyl group, an alkoxy group or an alkylthio group having 6 to 14 carbon atoms; X represents a hydrogen atom or a fluorine atom; Y represents a hydrogen atom or a methyl group; n is 0 or 1; Z represents a methyl group or a trifluoromethyl group; and R² represents an alkyl group having 2 to 8 carbon atoms.

2. The optically active 4-mercaptocinnamic acid derivative as claimed in claim 1, wherein R¹ represents an alkyl group having 6 to 14 carbon atoms; X represents a hydrogen atom; Y represents a hydrogen atom; n is 0 or 1; Z represents a methyl group; and R² represents an alkyl group having 2 to 8 carbon atoms.

3. A method of preparing an optically active 4-mercaptocinnamic acid derivative as claimed in claim 1, wherein a compound represented by general formula (2)

wherein R¹ represents an alkyl group, an alkoxy group or an alkylthio group having 6 to 14 carbon atoms; X represents a hydrogen atom or a fluorine atom; Y represents a hydrogen atom or a methyl group, or its reactive derivative, is condensed with an optically active compound represented by general formula (3)

wherein n is 0 or 1; Z represents a methyl group or a trifluoromethyl group; and R² represents an alkyl group having 2 to 8 carbon atoms.

4. A method of preparing an optically active 4-mercaptocinnamic acid derivative as claimed in claim 1, wherein a compound represented by general formula (4)

wherein $R^1$ represents an alkyl group, an alkoxy group or an alkylthio group having 6 to 14 carbon atoms, or its reactive derivative, is condensed with an optically active compound represented by general formula (5)

wherein X represents a hydrogen atom or a fluorine atom; Y represents a hydrogen atom or a methyl group; n is 0 or 1; Z represents a methyl group or a trifluoromethyl group; and $R^2$ represents an alkyl group having 2 to 8 carbon atoms.

5. A liquid crystal composition exhibiting bistability, comprising at least one optically active 4-mercaptocinnamic acid derivative as claimed in claim 1 or 2.

6. A liquid crystal composition exhibiting tristability, comprising at least one 4-mercaptocinnamic acid derivative as claimed in claim 1 or 2.

7. A liquid crystal device comprising said liquid crystal composition exhibiting bistability as claimed in claim 5.

8. A liquid crystal device comprising said liquid crystal composition exhibiting tristability as claimed in claim 6.

* * * * *